United States Patent [19]

Johnson, Jr.

[11] Plant 4,020

[45] Mar. 1, 1977

[54] STRAWBERRY PLANT

[75] Inventor: Harold A. Johnson, Jr., Watsonville, Calif.

[73] Assignee: Driscol Strawberry Associates, Inc., Watsonville, Calif.

[21] Appl. No.: 674,455

[22] Filed: Apr. 7, 1976

[51] Int. Cl.[2] ..... A01H 5/03

[52] U.S. Cl. ..... Plt./49

[58] Field of Search ..... Plt./48–49

*Primary Examiner*—Robert E. Bagwill

EXEMPLARY CLAIM

1. The new and distinct variety of strawberry plant herein described and illustrated, and identified by the characteristics enumerated above.

1 Drawing Figure

This invention relates to a new and distinct variety of strawberry plant which is the result of a cross of the patented everbearing variety known to Driscoll Strawberry Associates, Inc. as Selection E3, U.S. Plant Pat. No. 2,891, and Driscoll Strawberry Associates, Inc. Selection NM55.5.

The seedlings resulting from the aforementioned cross were grown and asexually multiplied in Shasta County, Calif. and tested in the fruiting beds on the property of growers of the Driscoll Strawberry Associates, Inc. Clones of the seedlings were also held at the Propagation Nursery in Shasta County. One plant was selected from the aforementioned group of seedlings and further asexually reproduced in the Shasta County nursery of Driscoll Strawberry Associates, Inc. Tests followed in various parts of California during intervening seasons on various properties of grower members of the Driscoll Strawberry Associates, Inc. These tests indicated the merits of the novel plant and resulted in its selection as a promising test variety.

FIG. 1 of the accompanying drawing illustrates plant parts of the new variety, typical in size, shape and color.

The inflorescence illustrates typical branching and relative size about the last of June. There is one secondary peduncle and one pedicel holding a secondary berry which is common. Most inflorescences have two secondary peduncles present and often three. The leaf shown is typical in appearance and size, but the petiole bract, which is not uncommon, is missing. The variation in the fruit shape illustrated is typical.

The plant of this new everbearing variety is medium in size, becoming larger and more vigorous during the fruiting season. This variety has the ability to give a large total production even when dug in late January or in February and transplanted in the central coast region of California. The transplant does require adequate chilling, however, before it can produce a vigorous enough plant to support a strong crop the same year it is planted.

The crown crop after being planted is medium in size, but the main crop which starts during the last of May and early June is better in size and remains medium to good in size through the late fall.

This novel plant of the present invention is distinguished from other varieties by its fruit and plant characteristics. In contrast to the Driscoll E18 variety, U.S. Plant Pat. No. 3,529, and other everbearers it becomes a stronger plant as the season progresses. It has the ability to survive adverse soil and pest conditions, plus the ability to produce a late fall crop in contrast to the E18. It also has the ability to not set more crop than it can support, helping it to maintain fruit size.

The leaves of this new variety have petioles that are longer than E18, but individual leaflets are near the same to slightly larger in size. Bracts are more often present on the petiole and petiolules are longer and the leaves are generally darker than E18. Older leaves of the new variety tend to lose color giving the plant a lighter appearance during the late fall.

The inflorescence of the new variety is longer than the E18 and the pedicel holding the primary berry originates at the axil of peduncles holding secondary berries more often than the E18. The fruit of the new variety is generally larger than E18, but not as consistent in shape or smoothness. Its dessert flavor is not as sweet to the taste as E18, but its aroma is equal to E18. The gloss and general appearance of the new variety is better than E18 even though its epidermis is not as firm and its seed is not as exerted as E18. It is more susceptible to Botrytis than E18, its large calyx which is more clasping than E18 contributes to its susceptibility to rot. Sepal serrations are usually more abundant on the new variety. The new variety is less susceptible to the two-spotted mite and is less sensitive to the phytotoxicity of pesticides than E18. At this point in its testing it appears to be suceptible to crown damaging organisms which contribute to the dying of young plants. The new variety has a greater field tolerance to two-spotted mite and Mycospharella leaf spot than E18. It is also more tolerant of powdery mildew than E18. It has not been completely tested against the Verticillium and Red Stele diseases. As a seedling it withstood the natural invasions of certain virus components found in central California without losing its ability to produce.

The varietal characteristics of the novel plant described below in detail were observed mainly during the first fruiting season, but reference is also made to the appearance during the second fruiting year. Observations were made in the Watsonville area of California which is a cool coastal area near the Pacific Ocean. The color terminology is in accordance with Ridgway's Color Standards and Nomenclature (1912 Edition). Observations were made mainly during July.

*Plants.*—Medium, becoming larger during the first year. Vigorous if given ample chilling and has an extensive root system, producing multiple crowns by the end of the first season.

*Leaves.*—Medium to large, 5 to 10 cm wide and 5 to 10 cm in length with the width usually equal to the length. Petioles abundant and long, mostly 15 to 20 cm in length. Petiolules are long, mostly 10 to 12 mm. Bracts are often present on petioles. Leaflets are rugose with puffiness between veins. Leaflet serrations are ovate often having a double apex. Leaflet color considered dark but may vary during the season with older leaves becoming lighter as the season progresses. Upper side of leaflet is Dark Cress Green, Plate XXXI.

*Runners.*—Medium in vigor, erratic in production both at the nursery and fruiting beds. Considered a poor runner producer.

*Inflorescence.*—Medium to long in length, 20 to 30 cm becoming longer as the season progresses. There may be 10 or more inflorescences per plant but the number of berries per inflorescence is not considered great. Mostly 2 to 3 secondary peduncles per inflorescence. Flowers are large and showy mainly during the first main crop; the plant tends to hide the inflorescence as the season progresses. Petals are mostly 5 to 6 in number. Anthers produce an abundance of pollen during the main fruiting period. Pedicels holding primary berries originate mainly at the axil formed by the union of secondary peduncles. Hair on pedicels 20 mm below tertiary flowers lies against and parallel with the pedicel.

*Fruit.*—Crown crop medium in size with the main crop medium to large. Not consistent in shape varying from long to short wedge with some primaries producing a multiple apex giving a cockscomb shape. Longitudinal furrows extending from the calyx to the apex are common. Shoulders of the fruit are large and rounded especially on primaries with the calyx often joining the berry at a point below the outline of the fruit when observing a berry from the side. This gives the calyx a reflexed appearance but much of the sepal is touching the fruit. Secondary and tertiary berries tend to be long wedge to long conic in outline, but shallow furrows are still common even though the surface is smoother than primaries. The apex may remain white, especially if the seed is unfertilized giving a seedy appearance at the tip. Primaries and secondaries may ripen at the same time. The skin is firm, but seed may be exerted, even with the surface, or slightly sunken. The seed is medium in size, yellow, but darkens when exposed to direct sun. The dessert quality is considered medium, not sweet to the taste. The skin color is Nopal Red, Plate I; the flesh is Scarlet, Plate I at the perimeter.

*Calyx.*—Large in diameter 40 to 45 mm on primaries. Often clasping the fruit surface but may be reflexed on primaries. Sepals on primaries are abundant 10 to 17 in number, serrated and overlap each other. Individual sepals are elliptical to ovate in outline, but have an acute apex. Color of the sepals on side facing fruit, Cress Green, Plate XXXI.

I claim:

1. The new and distinct variety of strawberry plant herein described and illustrated, and identified by the characteristics enumerated above.

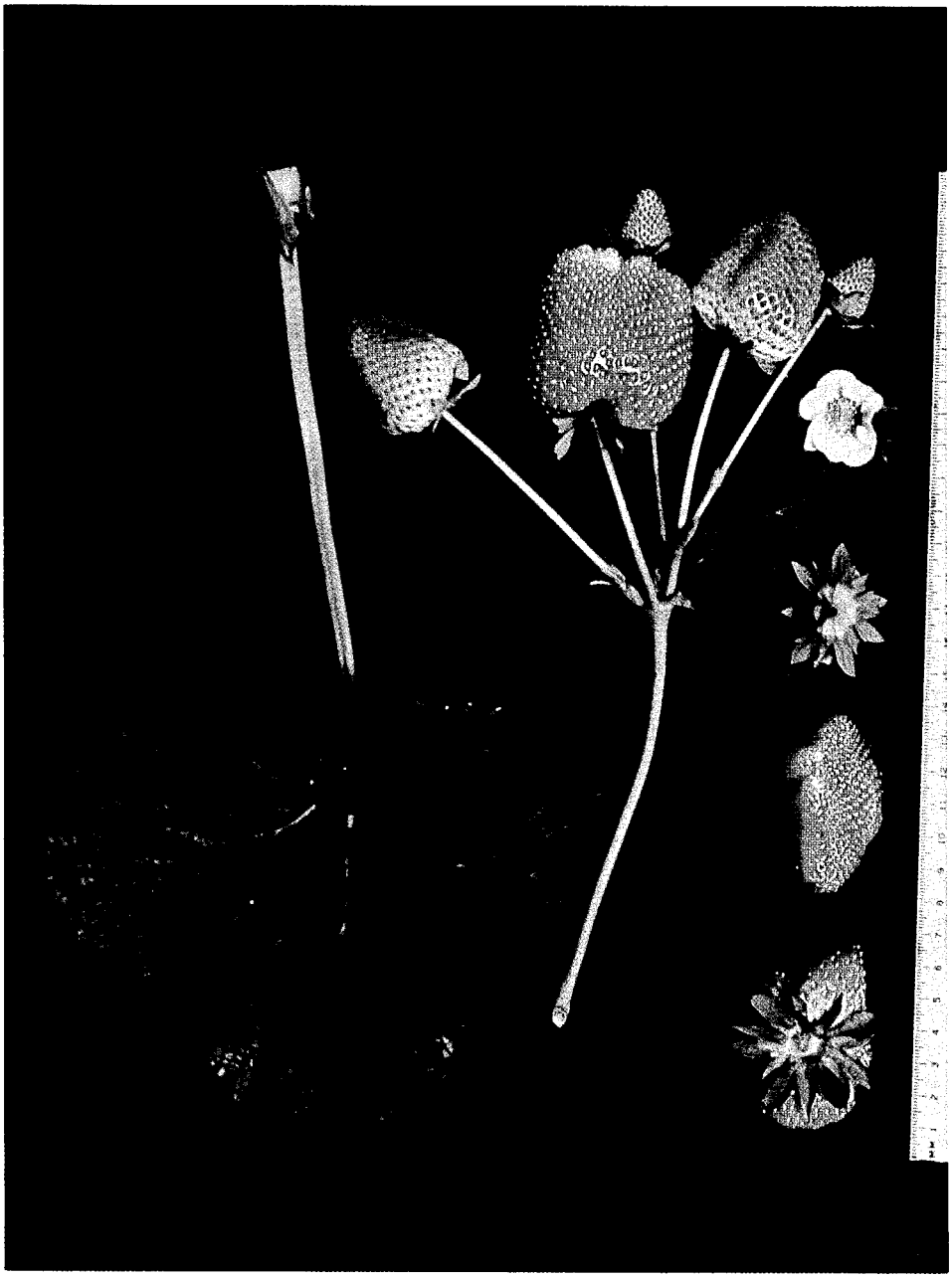

* * * * *